(12) United States Patent
Asada et al.

(10) Patent No.: US 8,324,271 B2
(45) Date of Patent: Dec. 4, 2012

(54) EYE DROP COMPOSITION CONTAINING ISOPROPYL UNOPROSTONE

(75) Inventors: Hiroyuki Asada, Osaka (JP); Akio Kimura, Osaka (JP)

(73) Assignee: R-Tech Ueno, Ltd., Tokyo (JP)

( * ) Notice: Subject to any disclaimer, the term of this patent is extended or adjusted under 35 U.S.C. 154(b) by 0 days.

(21) Appl. No.: 13/136,309

(22) Filed: Jul. 28, 2011

(65) Prior Publication Data

US 2011/0295034 A1 Dec. 1, 2011

Related U.S. Application Data

(62) Division of application No. 11/989,128, filed as application No. PCT/JP2006/315284 on Aug. 2, 2006, now Pat. No. 8,030,349.

(30) Foreign Application Priority Data

Aug. 2, 2005 (JP) ................................ 2005-223862

(51) Int. Cl.
*A61K 31/215* (2006.01)

(52) U.S. Cl. ......................... 514/530; 514/912; 514/913

(58) Field of Classification Search ........................ None
See application file for complete search history.

(56) References Cited

U.S. PATENT DOCUMENTS

| | | | |
|---|---|---|---|
| 4,305,947 A | 12/1981 | Bartner | |
| 5,631,287 A | 5/1997 | Schneider | |
| 5,767,154 A | 6/1998 | Woodward et al. | |
| 6,235,781 B1 | 5/2001 | Weiner et al. | |
| 6,281,224 B1 | 8/2001 | Miyagi et al. | |
| 6,486,208 B1 | 11/2002 | Castillo et al. | |
| 2002/0002185 A1 | 1/2002 | Reed et al. | |
| 2005/0228048 A1 | 10/2005 | Asada et al. | |

FOREIGN PATENT DOCUMENTS

| | | |
|---|---|---|
| JP | 02-311424 A | 12/1990 |
| JP | 2003-146881 A | 5/2003 |
| JP | 2003-327530 A | 11/2003 |
| JP | 2004-307491 A | 11/2004 |
| WO | WO 00/18316 A2 | 4/2000 |
| WO | WO 03/105847 A1 | 12/2003 |
| WO | WO 2004/013119 A1 | 2/2004 |
| WO | WO 2005/023258 A1 | 3/2005 |

OTHER PUBLICATIONS

Supplementary European Search Report dated Mar. 3, 2010 for European patent application EP 06 782 153.8.

Takagi et al., "Pharmaceutical characteristics of AFP-168 (tafluprost), a new prostanoid FP receptor agonist, as an ocular hypotensive drug," *Experimental Eye Research*, 78 (2004), pp. 767-777.

International Search Report dated Oct. 31 2006 for PCT/JP2006/315284.

*Primary Examiner* — Yong Chong
*Assistant Examiner* — Jody Karol
(74) *Attorney, Agent, or Firm* — Sughrue Mion, PLLC

(57) ABSTRACT

An eye drop composition in which the degradation of isopropyl unoprostone in an eye drop is prevented by adding trometamol to the eye drop containing isopropyl unoprostone.

1 Claim, No Drawings

EYE DROP COMPOSITION CONTAINING ISOPROPYL UNOPROSTONE

CROSS-REFERENCE TO RELATED APPLICATIONS

This application is a divisional application of application Ser. No. 11/989,128 filed Jan. 22, 2008 now U.S. Pat. No. 8,030,349, which is the United States national phase application under 35 USC 371 of International application PCT/JP2006/315284 filed Aug. 2, 2006. The entire contents of each of application Ser. No. 11/989,128 and International application PCT/JP2006/315284 are hereby incorporated by reference herein.

TECHNICAL FIELD

The present invention relates to a method for preventing the degradation of a thermally unstable medicament in an eye drop by adding an organic amine to the eye drop containing the thermally unstable medicament, and an eye drop composition in which the degradation of a thermally unstable medicament in an eye drop is prevented by adding an organic amine to the eye drop containing the thermally unstable medicament.

BACKGROUND ART

In an eye drop, a thermally unstable medicament, for example, a prostaglandin derivative such as latanoprost, isopropyl unoprostone, tafluprost or travoprost, an esterified steroid such as methylprednisolone sodium succinate or prednisolone acetate, a carboxylic acid ester such as ethyl parahydroxybenzoate, ethyl aminobenzoate, procaine or aspirin, or the like is sometimes added.

However, the storage temperature for an eye drop may sometimes increase during distribution or storage. In the case where a thermally unstable medicament is contained in an eye drop, when the medicament is degraded due to a rise of the storage temperature, a desired drug efficacy is not exhibited, and further, sometimes suspended matter may occur or the eye drop may become turbid. If it is stored in a cold place, the degradation of a thermally unstable medicament can be effectively prevented. However, an eye drop can be exposed to various environments, therefore, it is necessary to prevent the degradation of the medicament by a method other than the storage in a cold place.

On the other hand, it is general that a water-soluble organic amine is added to an eye drop as a buffer, however, the water-soluble organic amine is sometimes added for other purposes.

JP-A-2003-146881 discloses an invention relating to an anti-allergic ophthalmic preparation and describes that by adding an organic amine to an ophthalmic preparation containing pemirolast potassium (medicament), deposition of crystals of pemirolast potassium can be prevented. Further, JP-A-2003-327530 discloses an invention relating to an eye drop containing a tetrazole derivative and describes that by adding a basic amine compound, the preservative effect of a cationic preservative can be enhanced.

However, there is no report that by adding an organic amine to an eye drop containing a thermally unstable medicament, the medicament is stabilized thereby to prevent its degradation.

DISCLOSURE OF THE INVENTION

Problems to be Solved

It is desired that even if the storage temperature for an eye drop rises during distribution or storage, the degradation of a thermally unstable medicament contained in the eye drop is prevented thereby to stabilize the eye drop.

Means for Solving the Problems

The present inventors made intensive studies in order to prevent the degradation of a thermally unstable medicament and found that by adding an organic amine to an eye drop containing a thermally unstable medicament, the degradation of the medicament in the eye drop can be effectively prevented, and therefore the eye drop can be stably stored.

That is, the present invention is directed to:

(1) a method for preventing the degradation of a thermally unstable medicament in an eye drop by adding an organic amine to the eye drop containing the thermally unstable medicament;

(2) the method according to the above (1), wherein the thermally unstable medicament is a medicament which is easily thermally degraded;

(3) the method according to the above (2), wherein the medicament which is easily thermally degraded is a medicament which is easily thermally hydrolyzed;

(4) the method according to the above (1), wherein the thermally unstable medicament is a prostaglandin derivative;

(5) the method according to the above (4), wherein the prostaglandin derivative is latanoprost, isopropyl unoprostone, tafluprost or travoprost;

(6) the method according to the above (1), wherein the organic amine is an organic amine having a hydroxy group;

(7) the method according to the above (6), wherein the organic amine having a hydroxy group is trometamol;

(8) a method for preventing the degradation of latanoprost in an eye drop by adding trometamol to the eye drop containing latanoprost;

(9) an eye drop composition in which the degradation of a thermally unstable medicament in an eye drop is prevented by adding an organic amine to the eye drop containing the thermally unstable medicament;

(10) the eye drop composition according to the above (9), wherein the thermally unstable medicament is a medicament which is easily thermally degraded;

(11) the eye drop composition according to the above (10), wherein the medicament which is easily thermally degraded is medicament which is easily thermally hydrolyzed;

(12) the eye drop composition according to the above (9), wherein the thermally unstable medicament is a prostaglandin derivative;

(13) the eye drop composition according to the above (12), wherein the prostaglandin derivative is latanoprost, isopropyl unoprostone, tafluprost or travoprost;

(14) the eye drop composition according to the above (9'), wherein the organic amine is an organic amine having a hydroxy group;

(15) the eye drop composition according to the above (14), wherein the organic amine having a hydroxy group is trometamol; and

(16) an eye drop composition in which the degradation of latanoprost in an eye drop is prevented by adding trometamol to the eye drop containing latanoprost.

In the present invention, the thermally unstable medicament is not particularly limited as long as it is a medicament which has a tendency to be degraded in an eye drop when the temperature becomes higher than room temperature (25° C.), and examples of such a thermally unstable medicament include medicaments which have an ester bond and a tendency to be thermally hydrolyzed, for example, prostaglandin derivatives such as latanoprost, isopropyl unoprostone, tafluprost and travoprost, esterified steroids such as methylprednisolone sodium succinate and prednisolone acetate, carboxylic acid esters such as ethyl parahydroxybenzoate, ethyl aminobenzoate, procaine and aspirin, and the like, and particularly preferred are prostaglandin derivatives such as latanoprost, isopropyl unoprostone and travoprost.

The concentration of the thermally unstable medicament in an eye drop is not particularly limited as long as it is a concentration that allows the medicament to exhibit a desired drug efficacy, and for example, it is in the range of from 0.00001 to 10% (w/v).

The organic amine is not particularly limited as long as it is a water-soluble organic amine, and examples of the water-soluble organic amine include organic amines having a hydroxy group such as monoethanolamine, diethanolamine, triethanolamine, trometamol and meglumine, and more preferred are trometamol and meglumine.

The concentration of the organic amine in an eye drop is not particularly limited, however, for example, in the case of trometamol, it is preferably in the range of from 0.001 to 5% (w/v), more preferably from 0.005 to 3% (w/v).

The eye drop of the present invention can be prepared by a widely used method, and a tonicity agent, a buffer, a pH adjusting agent, a solubilizer, a viscosity-increasing agent or the like can be added, if necessary.

Examples of the tonicity agent include glycerin, propylene glycol, polyethylene glycol, trehalose, sucrose, sorbitol, mannitol, sodium chloride, potassium chloride, calcium chloride, magnesium chloride and the like.

Examples of the buffer include phosphates such as sodium phosphate, sodium dihydrogen phosphate, disodium hydrogen phosphate, potassium phosphate, potassium dihydrogen phosphate and dipotassium hydrogen phosphate; borates such as sodium borate and potassium borate; citrates such as sodium citrate and disodium citrate; acetates such as sodium acetate and potassium acetate; carbonates such as sodium carbonate, sodium hydrogen carbonate; and the like.

Examples of the pH adjusting agent include hydrochloric acid, citric acid, phosphoric acid, acetic acid, sodium hydroxide, potassium hydroxide, sodium carbonate, sodium hydrogen carbonate and the like.

Examples of the solubilizer include polysorbate 80, polyoxyethylene hydrogenated castor oil 60, macrogol 4000 and the like.

Examples of the viscosity-increasing agent include hydroxypropylmethyl cellulose, hydroxypropyl cellulose, polyvinyl alcohol, carboxyvinyl polymer, polyvinylpyrrolidone and the like.

The pH of the eye drop of the present invention is preferably in the range of from 3 to 9, particularly from 4 to 8.

Advantage of the Invention

By adding an organic amine to an eye drop containing a thermally unstable medicament, the degradation of the medicament in the eye drop can be effectively prevented, and therefore a stable eye drop can be provided.

BEST MODE FOR CARRYING OUT THE INVENTION

Heat Stability Test

By using latanoprost (chemical name: isopropyl-(Z)-7 [(1R,2R,3R,5S)3,5-dihydroxy-2-[(3R)-3-hydroxy-5-phenylpentyl]cyclopentyl]-5-heptanoate) as a thermally unstable medicament, a heat stability test was carried out.

(1) Sample Preparation

Formulation 1

1 g of trometamol was dissolved in about 80 mL of purified water, and the pH of the solution was adjusted to 7.0 with dilute hydrochloric acid. Then, the total volume was made up to 100 mL with purified water, whereby a vehicle was prepared. 100 mL of the resulting vehicle was added to 5 mg of latanoprost, and the mixture was stirred in a water bath at about 80° C. with heating thereby to dissolve latanoprost. After the temperature of the resulting solution was returned to room temperature, the pH of the solution was confirmed to be 7.0.

Comparative Formulation 1

1 g of sodium dihydrogen phosphate (a buffer) was dissolved in about 80 mL of purified water, and the pH of the solution was adjusted to 7.0 with 1 N sodium hydroxide. Then, the total volume was made up to 100 mL with purified water, whereby a vehicle was prepared. 100 mL of the resulting vehicle was added to 5 mg of latanoprost, and the mixture was stirred in a water bath at about 80° C. with heating thereby to dissolve latanoprost. After the temperature of the resulting solution was returned to room temperature, the pH of the solution was confirmed to be 7.0.

(2) Test Method and Results 5 mL of each of Formulation 1 and Comparative formulation 1 was filled in glass ampoules, which were stored at 80° C. for 4 weeks and at 50° C. for 8 weeks, respectively, for each formulation. Then, the content of latanoprost was determined using high performance liquid chromatography (HPLC), and the residual ratio thereof was calculated. The test results are shown in Table 1.

TABLE 1

|  | Residual ratio of latanoprost (%) | |
| --- | --- | --- |
|  | 80° C., 4 weeks | 50° C., 8 weeks |
| Sample 1 | 84% | 96% |
| Comparative sample 1 | 24% | 89% |

(3) Discussion

As is apparent from Table 1, the residual ratio of latanoprost in the eye drop (Sample 1) to which trometamol was added is larger than that in the eye drop (Comparative sample 1) to which sodium dihydrogen phosphate was added. Therefore, by adding an organic amine (trometamol) to an eye drop containing a thermally unstable medicament (latanoprost), the degradation of the thermally unstable medicament in the eye drop can be effectively prevented, and therefore the eye drop can be stably stored.

The invention claimed is:

1. An eye drop composition in which the degradation of isopropyl unoprostone in an eye drop is prevented by adding trometamol to the eye drop containing isopropyl unoprostone.

* * * * *